United States Patent
Woo et al.

(10) Patent No.: US 10,660,984 B2
(45) Date of Patent: *May 26, 2020

(54) ABSORBENT ARTICLE COMPRISING A MALODOR CONTROL COMPOSITION HAVING AN ACID CATALYST

(71) Applicant: The Procter & Gamble Company, Cincinnati, OH (US)

(72) Inventors: Ricky Ah-man Woo, Hamilton, OH (US); Steven Anthony Horenziak, Cincinnati, OH (US); Rhonda Jean Jackson, Cincinnati, OH (US); Zaiyou Liu, West Chester, OH (US); Michael-Vincent Nario Malanyaon, Indian Springs, OH (US); Jason John Olchovy, West Chester, OH (US); Christine Marie Readnour, Fort Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 475 days.

This patent is subject to a terminal disclaimer.

(21) Appl. No.: 15/583,341

(22) Filed: May 1, 2017

(65) Prior Publication Data

US 2017/0232135 A1    Aug. 17, 2017

Related U.S. Application Data

(63) Continuation-in-part of application No. 14/169,816, filed on Jan. 31, 2014, now Pat. No. 9,655,792, which
(Continued)

(51) Int. Cl.
*A61F 13/84* (2006.01)
*A61L 15/46* (2006.01)
(Continued)

(52) U.S. Cl.
CPC .......... *A61L 15/46* (2013.01); *A61F 13/8405* (2013.01); *A61L 9/01* (2013.01);
(Continued)

(58) Field of Classification Search
CPC ............ A61F 13/8405; A61F 13/51113; A61F 2013/51076; A61F 2013/5109;
(Continued)

(56) References Cited

U.S. PATENT DOCUMENTS 7,799,966 B2    9/2010  Williams et al.
9,655,792 B2 *  5/2017  Woo .......................... A61L 9/01
(Continued)

FOREIGN PATENT DOCUMENTS

EP    1884251    2/2008

OTHER PUBLICATIONS

PCT International Search Report, dated Mar. 24, 2011, 5 pages.

*Primary Examiner* — Catharine L Anderson
(74) *Attorney, Agent, or Firm* — William E. Gallagher; Andres E. Velarde (57) ABSTRACT

An absorbent article comprising a complexed or encapsulated malodor control composition having at least one volatile aldehyde and an acid catalyst, and methods of use thereof, are provided. The malodor control composition is suitable for a variety of absorbent articles, including use in diapers, toddler training pants, adult incontinence garments, sanitary napkins, pantiliners, interlabial devices, hemorrhoid pads, and the like.

20 Claims, 1 Drawing Sheet

Related U.S. Application Data is a continuation of application No. 12/970,098, filed on Dec. 16, 2010, now Pat. No. 8,674,167.

(60) Provisional application No. 61/287,369, filed on Dec. 17, 2009.

(51) Int. Cl.
  *A61L 9/01* (2006.01)
  *A61L 15/20* (2006.01)
  *A61L 9/015* (2006.01)
  *A61L 9/04* (2006.01)
  *A61L 9/014* (2006.01)
  *A61F 13/51* (2006.01)

(52) U.S. Cl.
  CPC ............... *A61L 9/014* (2013.01); *A61L 9/015* (2013.01); *A61L 9/044* (2013.01); *A61L 15/20* (2013.01); *A61F 2013/5109* (2013.01); *A61F 2013/51076* (2013.01); *A61F 2013/8408* (2013.01); *A61L 2209/21* (2013.01); *A61L 2300/21* (2013.01); *A61L 2300/216* (2013.01); *A61L 2300/45* (2013.01)

(58) Field of Classification Search
  CPC ...... A61F 2013/8408; A61F 2013/8411; A61F 2013/8435; A61L 15/46
  See application file for complete search history.

(56) References Cited

U.S. PATENT DOCUMENTS

| | | |
|---|---|---|
| 2003/0158079 A1 | 8/2003 | Dykstra et al. |
| 2004/0082928 A1 | 4/2004 | Pesce et al. |
| 2005/0075617 A1 | 4/2005 | Vartiainen |
| 2008/0071238 A1 | 3/2008 | Sierri et al. |

* cited by examiner

ABSORBENT ARTICLE COMPRISING A MALODOR CONTROL COMPOSITION HAVING AN ACID CATALYST

FIELD OF THE INVENTION

The present invention relates to an absorbent article comprising a malodor control composition having at least one volatile aldehyde and an acid catalyst, and methods of use. The malodor control composition is suitable for use in a variety of absorbent articles, including diapers, toddler training pants, adult incontinence garments, sanitary napkins, pantiliners, interlabial devices, hemorrhoid pads, and the like.

BACKGROUND OF THE INVENTION

Products for reducing or masking malodors are well known in the art and are widely described in patent literature. These products may be designed to work specifically in air or on fabrics or other surfaces. See, e.g., U.S. Pat. Nos. 5,942,217; 5,955,093; and 6,033,679. However, not all odors are effectively controlled by products on the market, such as amine-based malodors associated with urine and sulfur-based malodors associated with bodily fluids and excrements such as menses and feces, which are difficult to combat. Further, the time required for a composition to noticeably combat malodors may create consumer doubt as to a product's efficacy on malodors. For example, the malodor may become noticeable to a consumer of the product before the product begins to noticeably reduce the malodor.

In the context of absorbent articles, previous attempts have been made to develop compositions for incorporation in absorbent article to control malodor associated with bodily fluids and excrement, such as urine, menses, and feces. Some known malodor control compositions provide an overwhelming perfume scent to the product that may not be acceptable to some consumers. There thus still remains a desire to provide an improved malodor control composition for incorporation into an absorbent article product.

There remains a need for a fast acting malodor control composition that neutralizes malodors and is effective on a broad range of malodors, including amine-based and sulfur-based malodors, while not overpowering malodors with an overwhelming perfume.

SUMMARY OF THE INVENTION

The present invention encompasses an absorbent article comprising a complexed or encapsulated malodor control composition comprising at least one volatile aldehyde; and an acid catalyst having a vapor pressure of about 0.01 to about 13 at 25° C.

The present invention further encompasses a method of neutralizing malodor comprising contacting the malodor with a malodor control composition comprising at least one volatile aldehyde; and an acid catalyst having a vapor pressure of about 0.01 to about 13 at 25° C.

DETAILED DESCRIPTION OF THE INVENTION

The present invention relates to a malodor control composition having at least one volatile aldehyde and an acid catalyst for neutralizing malodors, and methods thereof.

"Malodor" refers to compounds generally offensive or unpleasant to most people, such as the complex odors associated with bowel movements (i.e. feces) or other bodily excrements or fluids.

"Neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Odor neutralization may be distinguished from odor masking or odor blocking by a change in the malodorous compound, as opposed to a change in the ability to perceive the malodor without any corresponding change in the condition of the malodorous compound.

"Absorbent article" refers to devices that absorb and contain body exudates, such as urine, menses, and feces. The term "disposable" is used herein to describe absorbent articles which are not intended to be laundered or otherwise restored or reused as an absorbent article after a single use. Examples of absorbent articles include diapers, toddler training pants, adult incontinence garments, and feminine hygiene garments such as sanitary napkins, pantiliners, interlabial devices, hemorrhoid pads, and the like.

Absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side and is intended to be worn toward or placed adjacent to the wearer's undergarments when the disposable absorbent article is worn.

The complexed or encapsulated compound of the present invention can be disposed in various locations in the absorbent article. In the case of paper towels, wipes, toilet paper and facial tissues the compound can be applied on any surface of any of the layers making up the article or be mixed with the cellulose fibers during the making process.

In the case of absorbent hygienic articles the complexed or encapsulated compound can be disposed on the garment-facing side or the body-facing side of the topsheet or absorbent core, or on the body-facing side of the backsheet. Preferably, the complexed or encapsulated compound is disposed on the absorbent core, and preferably on the body-facing side of the absorbent core. The complexed or encapsulated compound can also be disposed on other components of the absorbent article, when present, such as the garment-facing side or body-facing side of a secondary topsheet or acquisition layer.

In certain embodiments the complexed or encapsulated compound of the present invention is disposed in the absorbent article in a layer that is closer to the body-facing surface of the absorbent article than the absorbent core or a layer comprising superabsorbent material (e.g. absorbent gelling material ("AGM")). In some cases in order for the complexed or encapsulated compound to effectively release the compound it needs to come in contact with moisture. A problem exists when incorporating a complexed or encapsulated compound in an absorbent hygienic article, because other components, such as the absorbent core and/or superabsorbent material, of the absorbent article have a strong affinity for bodily fluids, including the moisture contained therein. When an absorbent article is insulted with bodily fluid, such as menses or urine, the complexed or encapsulated compound is thus in competition with the absorbent core and/or superabsorbent material for the moisture contained in the bodily fluid. The absorbent core and/or superabsorbent material has a strong affinity for the moisture and once the absorbent core and/or superabsorbent material contacts the bodily fluid, the absorbent core and/or superabsorbent material effectively "lock-up" the moisture of the bodily fluid, thereby reducing the amount of moisture available to contact the complexed or encapsulated compound and release the compound to provide odor control benefits. In these cases disposing the complexed or encapsulated compound in the absorbent article in a layer that is closer to the body-facing surface of the absorbent article than the absorbent core and/or a layer comprising superabsorbent material enables the complexed or encapsulated compound to come in contact with the bodily fluid preferentially before the bodily fluid comes into contact with the absorbent core and/or superabsorbent material. This results in more effective release of the compound and provides improved odor control benefits.

In the case of catamenial tampons the complexed or encapsulated compound can be present in any component of the tampon, including the absorbent compressed pledget forming the tampon body, the overwrap, and the extraction cord. For example it can be comprised in the tampon body, or on the tampon surface or, if an overwrap is present, on either surface of the overwrap. In case a secondary mass of absorbent material is present along the extension cord proximal to the extraction end of the tampon, the complexed or encapsulated compound can be comprised within this secondary mass.

Absorbent Article

In general, the absorbent articles of the present invention typically comprise a topsheet, a backsheet, and an absorbent core disposed between the topsheet and backsheet.

The topsheet of the absorbent article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet can also be vapor permeable ("breathable"), while remaining fluid impermeable. The backsheet may comprise a woven or nonwoven material, polymeric films such as thermoplastic films of polyethylene or polypropylene, or composite materials such as a film-coated nonwoven material.

The backsheet and the topsheet can positioned adjacent the garment surface and the body surface, respectively, of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa. The absorbent core can comprise superabsorbent materials such as absorbent gelling materials (AGM), including AGM fibers, as is known in the art.

The absorbent article can comprise other additional components, for example between the topsheet and absorbent core, such as a secondary topsheet or acquisition layer. The secondary topsheet or acquisition layer can comprise a tissue layer or a nonwoven, such as carded resin-bonded nonwovens, embossed carded resin-bonded nonwovens, high-loft carded resin-bonded nonwovens, carded through-air-bonded nonwovens, carded thermo-bonded nonwovens, spunbonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application.

The absorbent article can comprise further components such as side cuffs, typically found in diapers, or side wings or side flaps, typically found in sanitary napkins.

The absorbent articles herein are preferably disposable after a single use.

The malodor control composition of the present invention can be disposed in various locations in the absorbent article. The malodor control composition can be disposed on the garment-facing side or the body-facing side of the topsheet or absorbent core, or the body-facing side of the backsheet. Preferably, the malodor control composition is disposed on the absorbent core, and preferably on the garment-facing side of the absorbent core. The malodor control composition can also be disposed on other components, when present in the absorbent article, such as the garment-facing side or body-facing side of a secondary topsheet or acquisition layer.

Encapsulating Compounds

The reactive compounds of the present invention can be encapsulated using any technique known in the art. The term "Encapsulation" within the present invention is intended to encompass any technology which allows introducing a reactive compound according to the invention into an absorbent article as a solid in a mixture with other materials which are called in general "encapsulating materials". The reactive compounds when encapsulated are prevented from contacting other materials so to avoid unwanted reactions. Moreover, when encapsulated, their evaporation is prevented. Many types of capsules are known in the art and are used for the delivery of perfume ingredients. All these types of capsules are usable in the present invention. Capsules can have any size, typically used in the art and suitable herein are are nanocapsules, microcapsules, and larger capsules. In general capsules will have a size such that their shorter diameter will be lower than 3 mm or lower than 1 mm.

Capsules allow the encapsulated composition to release when it is needed. Typically in the case of absorbent articles this corresponds to two cases:

1—when the article receives a liquid insult (e.g. when in absorbent hygienic articles menses or urine are discharged): in this case capsules comprise water soluble materials or materials which trigger release of the encapsulated compound when contacted with water or a water containing liquid.

2—when pressure or force is exerted on the article (e.g. in the case of paper towels and wipes, or in the case when an absorbent hygienic article is worn during a period of high activity): in this case, for example, breakable capsules having a shell of rupturable polymeric film can be used.

All these types of capsule are known in the art e.g. as perfume delivery systems.

These two cases should however be intended as non limiting examples. In fact any other trigger (or combination of triggers) can be used to release the encapsulated compound from the capsule, e.g. evaporation, diffusion, temperature, humidity, light etc. The release of the encapsulated compound can be instantaneous or sustained over time, depending on needs. The skilled person, based on the desired trigger action and release type, will be able to select the appropriate encapsulating material from those known in the art.

Capsules can use different encapsulating materials:
I. Polymers. Polymeric materials can be used as encapsulating materials.
Classical coacervates, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. Polymeric capsules include but are not limited to:
a.) Matrix Systems: The compound to be encapsulated is dissolved or dispersed in a polymer matrix or particle. Such compounds, for example, may be dispersed into the polymer prior to formulating into the product. Diffusion of the encapsulated compound from the polymer is a common trigger that allows or increases the rate of compound release from a polymeric matrix system that is deposited or applied to the desired surface, although many other triggers are know that may control compound release. Absorption and/or adsorption into or onto polymeric particles, films, solutions, and the like are aspects of this technology. Nano- or micro-particles composed of organic materials (e.g., latexes) are examples. Suitable particles which can be used herein include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded compound associated with the polymer until the moment or moments of release. Such polymers may also suppress the neat product odor and provide a bloom and/or longevity benefit depending on the rate of compound release. One challenge with such systems is to achieve the ideal balance between 1) in-product stability (keeping the compound inside carrier until you need it) and 2) timely release (during use. Suitable micro-particles and micro-latexes as well as methods of making same may be found in USPA 2005/0003980 A1. Matrix systems also include hot melt adhesives and perfumed plastics. Polymer Assisted Delivery (PAD) matrix systems may include those described in the following references: US Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as encapsulating materials and can provide compound release benefits. Suitable silicones as well as making same may be found in WO 2005/102261; USPA 20050124530A1; USPA 20050143282A1; and WO 2003/015736. Functionalized silicones may also be used as described in USPA 2006/003913 A1. Examples of silicones include polydimethylsiloxane and polyalkyldimethylsiloxanes.

b.) Reservoir Systems: Reservoir systems are also known as a core-shell type technology, in which the compound to be released is surrounded by a release controlling membrane, which serves as a protective shell. The material inside the capsule is referred to as the core, internal phase, or fill, whereas the wall is sometimes called a shell, coating, or membrane. Depending on the type of shell materials the capsules can be activated by different mechanisms, for example the coating can be soluble in water or soluble in water solutions having a certain pH. In certain embodiments of the present invention the reservoir capsules have water insoluble shells and the core of the capsule is released upon mechanical activation.

Pressure sensitive capsules or friable capsules are examples of this technology. Friable capsules can be made in any sizes, and shapes, typically used are friable microcapsules. Any type of polymeric material can be used to make the shell of friable capsules, as well as any material can be used as a core material as known in the art. A skilled person will be able to determine which materials can be used to encapsulate certain core materials based on the knowledge available in the art concerning the compatibility of the materials (e.g. in general the shell material is selected so that core material will not act as a solvent on it). Friable microcapsules will be described now in more detail, it is clear to the skilled person that the same type of materials and construction can be used to make larger or smaller capsules.

Friable microcapsules are capsules where the outer shell is made from any polymer or mixture of polymers. Typical polymers which can be used to be comprised in the shell of a friable microcapsule include melamine-formaldehyde or urea-formaldehyde condensates, melamine-resorcinol or urea-resorcinol condensates, nylon, polyacrylates, polyethylenes, polyamides, polyamides, polystyrenes, polyisoprenes, polycarbonates, polyesters, polyureas, polyurethanes, polyolefins, polysaccharides, epoxy resins, vinyl polymers, silk, wool, gelatin, cellulose, proteins and mixture thereof as well as co-polymers comprising, as co monomers, monomers contained in these mentioned polymers.

Among the most stable friable microcapsules are those comprising polyoxymethyleneurea (PMU)-based polymers, melamine-formaldehyde based polymers, and polyacrylate based polymers.

In some embodiments the microcapsule outer shell material can include a polyacrylate material. Any polymer or copolymer including acrylate or metacrylate monomers can be used in the present invention, preferred materials are those known in the art as forming polyacrylate microcapsules such as, for example, those described in US2012-276210A1. In some embodiments the shell of the microcapsules comprises a polyacrylate copolymer, in some case can be a polyacrylate random copolymer.

A friable microcapsule is configured to release its core substance when its outer shell is ruptured. The rupture can be caused by forces applied to the outer shell during mechanical interactions. Friable microcapsules can have various fracture strengths. Each microcapsule can have an outer shell with a fracture strength of 0.2-10.0 mega Pascals, when measured according to the Fracture Strength Test Method, described in application U.S. 61/703,587. As an example, a microcapsule can have an outer shell with a fracture strength of 0.2-2.0 mega Pascals.

Friable microcapsules can have various core to outer shell ratios. Each microcapsule has an outer shell, and a core within the outer shell, and a core to outer shell ratio (in weight) from 99-1 to 1-99, or from 95-5 to 10-90, or from 50-50 to 90-10.

Friable microcapsules can have various outer shell thicknesses. In some embodiments the microcapsule can have an outer shell with an overall thickness of 1-300 nanometers or 2-200 nanometers.

For application to an anhydrous product such as an absorbent article, it is especially preferred that the microcapsule is applied as an anhydrous particle. Such particles may be produced by spray drying as describe in patent application U.S. 61/703,616. In the instances where friable microcapsules are spray dried, it is preferable to apply these particles in a paste or slurry comprising a carrier vehicle. These particles may also be directly applied to the substrate as a powder without using a carrier vehicle. It is for example possible to apply the spray dried particles to an adhesive that is part of a peelable surface containing an adhesive. Examples of peelable surfaces containing adhesives may include for example the panty fastening backsheet adhesive or the wings adhesive, such that when a consumer peels back the surface, a burst of fragrance is delivered to consumers and the fragrance can then be transferred to the clothing for added odor protection.

Alternately, the friable microcapsules can be delivered via an aqueous slurry to surfaces of the absorbent article and allowed to dry.

Friable microcapsules and relative methods for making them as well as methods to measure their properties which can be used herein are described in applications U.S. 61/703,616 and U.S. 61/703,587. which are incorporated herein by reference.

Example methods for making polyacrylate microcapsules are disclosed in U.S. Patent Application 61/328,949; U.S. Patent Application 61/328,954; U.S. Patent Application 61/328,962; and U.S. Patent Application 61/328,967. which are incorporated herein by reference.

II. Starches: The use of a starch encapsulation technology allows one to modify the properties of the compound to be encapsulated, for example, by converting a liquid compound into a solid by adding ingredients such as starch. The benefit includes increased retention for volatile compounds during product storage. Upon exposure to moisture, a release may be triggered. Another benefit is that the starch encapsulation allows the product formulator to select compounds or concentration of compounds that normally cannot be used without the presence of starch encapsulation. Suitable starch encapsulation examples as well as methods of making the same may be found in US 2005/0003980 A1 and U.S. Pat. No. 6,458,754 B1.

In one aspect, starch encapsulated compounds may be made by preparing a mixture comprising starch, water, acid and the compound(s) which need to be encapsulated, the acid being incorporated in the mixture in an amount sufficient to lower the pH of the starch-water mixture by at least 0.25 units; and spray drying the mixture thereby forming the encapsulated compound(s). In the first step in the process of compound(s) encapsulation, an aqueous mixture is prepared comprising starch, water, the compound(s) which need to be encapsulated and acid. These ingredients may be added in any order, but usually the starch-water mixture is prepared first and subsequently, either sequentially or together, the acid and compound(s) to encapsulate are added. When they are added sequentially, the acid may be added prior to the ingredient for encapsulation. Alternatively, the acid is added after the ingredient for encapsulation. The concentration of starch in the aqueous mixture may be from as low as 5 or 10 wt % to as high as 60 or even 75 wt %. Generally the concentration of starch in the mixture is from 20 to 50 wt %, more usually around 25 to 40 wt % in the aqueous mixture.

Suitable starches can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch and mixtures thereof. Modified starches may be particularly suitable for use in the present invention, and these include hydrolyzed starch, acid thinned starch, starch having hydrophobic groups, such as starch esters of long chain hydrocarbons ($C_5$ or greater), starch acetates, starch octenyl succinate and mixtures thereof. In one aspect, starch esters, such as starch octenyl succinates are employed.

The term "hydrolyzed starch" refers to oligosaccharide-type materials that are typically obtained by acid and/or enzymatic hydrolysis of starches, preferably corn starch. It may be preferred to include in the starch water-mixture, a starch ester. Particularly preferred are the modified starches comprising a starch derivative containing a hydrophobic group or both a hydrophobic and a hydrophilic group which has been degraded by at least one enzyme capable of cleaving the 1,4 linkages of the starch molecule from the non-reducing ends to produce short chained saccharides to provide high oxidation resistance while maintaining substantially high molecular weight portions of the starch base. The aqueous starch mixture may also include a plasticizer for the starch. Suitable examples include monosaccharides, disaccharides, oligosaccharides and maltodextrins, such as glucose, sucrose, sorbitol, gum arabic, guar gums and maltodextrin.

The acid used in the process of the invention may be any acid. Examples include sulfuric acid, nitric acid, hydrochloric acid, sulfamic acid and phosphonic acid. In one aspect, carboxylic organic acids are employed. In another aspect, organic acids comprising more than one carboxylic acid groups are employed. Examples of suitable organic acids include citric acid, tartaric acid, maleic acid, malic acid, succinic acid, sebacic acid, adipic acid, itaconic acid, acetic acid and ascorbic acid, etc. In one aspect, saturated acids, such as citric acid, are employed.

Following the formation of the aqueous mixture comprising starch, water, perfumes and acid, the mixture is mixed under high shear to form an emulsion or dispersion of ingredient for encapsulation in the aqueous starch solution.

Any suitable technique may then be used for the final stage of processing where the aqueous mixture including acid and perfumes is atomized and dried. Suitable techniques include, but are not limited to those known in the art including spray drying, extrusion, spray chilling/crystallization methods, fluid bed coating and the use of phase transfer catalysts to promote interfacial polymerization. Spray efficiencies may be increased by methods known in the art, such as by using high drying towers, lightly oiling the chamber walls, or using preconditioned air in which the moisture has been substantially removed.

Coated Capsules

In some embodiments the primary materials forming the capsule as described so far, may be further encapsulated with a secondary coating material. Any of the capsule types mentioned so far can be used in the present invention as such or with an additional secondary coating material.

An additional secondary coating material can help in reducing the scent perception, in reducing evaporation of volatile components over time (especially at elevated temperatures and humidity conditions) and in increasing chemical stability of the complexed compound by reducing the exposure of the complexed compounds (which in the present invention comprise highly reactive materials) to prematurely react or decompose so they are no longer functional or have a different odor character when activated. Additionally the use of coated capsules can allow altering the release characteristic of the encapsulated material (slowing or accelerating its release, or changing the release trigger, for example introducing a pH trigger). Generally, any second material that is added to or applied directly to a primary encapsulating material that accomplishes one or more of the above functions is characterized as a coating. The secondary coating may be directly applied using a second process step following creation of the primary capsule, using a process such as prilling, or using any fluidized bed process to apply a secondary surface coating (for example a Wurster Coater).

Coating compositions which are suitable for the present invention are all capsule coating compositions which are commonly known in the art. These include for example: polysaccharides (for example, but not limited to unmodified starch, chemically modified starch, dextrins, cyclodextrin and cyclodextrin derivatives), natural and artificial/synthetic waxes, esters and ester derivatives, fatty acids, natural and synthetic and chemically modified lipids, fatty alcohols, hydrocarbons (liner or branched, petrolatum), enteric coating compositions (such as the Eudragit series of Methacrylic acid co-polymers), polyvinyl alcohols, polyethylene glycols, silicones (for example, but not limited to silicone copolymers and functionalized silicones), surfactants, emulsifiers, polypropylene glycols, cellulose derivatives (methyl cellulose, hydroxypropyl cellulose), glycerin, mono and diglycerides, polyglycerol and polyglycerol esters and emulsifiers employed in food applications.

An example of the preparation of a coated capsule which can be used in the present invention has been described in U.S. Pat. No. 4,973,422 (see in particular Example 2).

Complexed Compounds

For "complex" it is intended an "inclusion complex" within the meaning of IUPAC Compendium of Chemical Terminology 2nd Edition (1997) wherein the complexing agent is the host and the complexed compound is the "guest". Examples of complexing agents are cyclodextrins. As used herein, the term "cyclodextrin" includes any of the known cyclodextrins such as substituted and unsubstituted cyclodextrins containing from about six to about twelve glucose units, for example alpha-cyclodextrin, beta-cyclodextrin, gamma-cyclodextrin and/or their derivatives and/or mixtures thereof. For example, the cyclodextrin complex of the present invention can comprise cyclodextrin selected from the group consisting of beta-cyclodextrin, alpha-cyclodextrin, hydroxypropyl alpha-cyclodextrin, hydroxypropyl beta-cyclodextrin, methylated-alpha-cyclodextrin, methylated-beta-cyclodextrin, and mixtures thereof. Cyclodextrin complexes of compounds which are active against malodors can be prepared as known in the art for example using the kneading method described in U.S. Pat. Nos. 5,571,782 and 5,543,157 or, preferably, using the spray drying method described in WO2008/104690A2.

Malodor Control Composition

The malodor control composition includes a mixture of volatile aldehydes and is designed to deliver genuine malodor neutralization and not function merely by covering up or masking odors. A genuine malodor neutralization provides a sensory and analytically measurable (e.g. gas chromatograph) malodor reduction. Thus, if the malodor control composition delivers a genuine malodor neutralization, the composition will reduce malodors in the vapor and/or liquid phase.

1. Volatile Aldehydes

The malodor control composition includes a mixture of volatile aldehydes that neutralize malodors in vapor and/or liquid phase via chemical reactions. Such volatile aldehydes are also called reactive aldehydes (RA). Volatile aldehydes may react with amine-based odors, following the path of Schiff-base formation. Volatiles aldehydes may also react with sulfur-based odors, forming thiol acetals, hemi thiolacetals, and thiol esters in vapor and/or liquid phase. It may be desirable for these vapor and/or liquid phase volatile aldehydes to have virtually no negative impact on the desired perfume character of a product. Aldehydes that are partially volatile may be considered a volatile aldehyde as used herein.

Suitable volatile aldehydes may have a vapor pressure (VP) in the range of about 0.0001 torr to 100 torr, alternatively about 0.0001 torr to about 10 torr, alternatively about 0.001 torr to about 50 torr, alternatively about 0.001 torr to about 20 torr, alternatively about 0.001 torr to about 0.100 torr, alternatively about 0.001 torr to 0.06 torr, alternatively about 0.001 torr to 0.03 torr, alternatively about 0.005 torr to about 20 torr, alternatively about 0.01 torr to about 20 torr, alternatively about 0.01 torr to about 15 torr, alternatively about 0.01 torr to about 10 torr, alternatively about 0.05 torr to about 10 torr, measured at 25° C.

The volatile aldehydes may also have a certain boiling point (B.P.) and octanol/water partition coefficient (P). The boiling point referred to herein is measured under normal standard pressure of 760 mmHg. The boiling points of many volatile aldehydes, at standard 760 mm Hg are given in, for example, "Perfume and Flavor Chemicals (Aroma Chemicals)," written and published by Steffen Arctander, 1969.

The octanol/water partition coefficient of a volatile aldehyde is the ratio between its equilibrium concentrations in octanol and in water. The partition coefficients of the volatile aldehydes used in the malodor control composition may be more conveniently given in the form of their logarithm to the base 10, log P. The log P values of many volatile aldehydes have been reported. See, e.g., the Pomona92 database, available from Daylight Chemical Information Systems, Inc. (Daylight CIS), Irvine, Calif. However, the log P values are most conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each volatile aldehyde, and takes into account the numbers and types of atoms, the atom connectivity, and chemical bonding. The C log P values, which are the most reliable and widely used estimates for this physicochemical property, are preferably used instead of the experimental log P values in the selection of volatile aldehydes for the malodor control composition.

The C log P values may be defined by four groups and the volatile aldehydes may be selected from one or more of these groups. The first group comprises volatile aldehydes that have a B.P. of about 250° C. or less and C log P of about 3 or less. The second group comprises volatile aldehydes that have a B.P. of 250° C. or less and C log P of 3.0 or more. The third group comprises volatile aldehydes that have a B.P. of 250° C. or more and C log P of 3.0 or less. The fourth group comprises volatile aldehydes that have a B.P. of 250° C. or more and C log P of 3.0 or more. The malodor control composition may comprise any combination of volatile aldehydes from one or more of the C log P groups.

In some embodiments, the malodor control composition of the present invention may comprise, by total weight of the malodor control composition, from about 0% to about 30% of volatile aldehydes from group 1, alternatively about 25%; and/or about 0% to about 10% of volatile aldehydes from group 2, alternatively about 10%; and/or about 10% to about 30% of volatile aldehydes from group 3, alternatively about 30%; and/or about 35% to about 60% of volatile aldehydes from group 4, alternatively about 35%.

Exemplary volatile aldehydes which may be used in a malodor control composition include, but are not limited to, Adoxal (2,6,10-Trimethyl-9-undecenal), Bourgeonal (4-t-butylbenzenepropionaldehyde), Lilestralis 33 (2-methyl-4-t-butylphenyl)propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3-cyclohexen-1-carbaldehyde), Florhydral (3-(3-Isopropyl-phenyl)-butyraldehyde), Citronellal (3,7-dimethyl 6-octenal), Cymal, cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional (alpha-methyl-3,4-(methylenedioxy)-hydrocinnamaldehyde, hydrocinnamaldehyde (3-phenylpropanal, 3-phenylpropionaldehyde), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolylproionaldehyde, 4-dimethylbenzenepropanal), Lyral (4-(4-hydroxy-4-methyl pentyl)-3-cyclohexene-1-carboxaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupical, tricyclodecylidenebutanal (4-Tricyclo5210-2,6decylidene-8butanal), Melafleur (1,2,3,4,5,6,7,8-octahydro-8,8-dimethyl-2-naphthaldehyde), Methyl Octyl Acetaldehyde, aldehyde C-11 MOA (2-methyl deca-1-al), Onicidal (2,6,10-trimethyl-5,9-undecadien-1-al), Citronellyl oxyacetaldehyde, Muguet aldehyde 50 (3,7-dimethyl-6-octenyl) oxyacetaldehyde), phenylacetaldehyde, Mefranal (3-methyl-5-phenyl pentanal), Triplal, Vertocitral dimethyl tetrahydrobenzene aldehyde (2,4-dimethyl-3-cyclohexene-1-carboxaldehyde), 2-phenylproprionaldehyde, Hydrotropaldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), and Precylcemone B (1-cyclohexene-1-carboxaldehyde).

Still other exemplary aldehydes include, but are not limited to, acetaldehyde (ethanal), pentanal, valeraldehyde, amylaldehyde, Scentenal (octahydro-5-methoxy-4,7-Methano-1H-indene-2-carboxaldehyde), propionaldehyde (propanal), Cyclocitral, beta-cyclocitral, (2,6,6-trimethyl-1-cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Lauric aldehyde, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, Trifernal, beta methyl Benzenepropanal, 2,6,6-Trimethyl-1-cyclohexene-1-acetaldehyde, phenyl Butenal (2-phenyl 2-butenal), 2.Methyl-3(p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenyl-propenoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H (alpha-n-hexyl-cinnamaldehyde), Floralozone, (para-ethyl-alpha,alpha-dimethyl Hydrocinnamaldehyde), Acalea (p-methyl-alpha-pentylcinnamaldehyde), methylcinnamaldehyde, alpha-Methylcinnamaldehyde (2-methyl 3-phenypropenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4(1-methylethenyl)-1-cyclohexene-1-carboxaldehyde), 2,4-Dimethyl-3-cyclohexene carboxaldehyde, 2-Methyl-2-pentenal, 2-methylpentenal, pyruvaldehyde, formyl Tricyclodecan, Mandarin aldehyde, Cyclemax, Pino acetaldehyde, Corps Iris, Maceal, and Corps 4322.

In one embodiment, the malodor control composition includes a mixture of two or more volatile aldehydes selected from the group consisting of 2-ethoxy Benzylaldehyde, 2-isopropyl-5-methyl-2-hexenal, 5-methyl Furfural, 5-methyl-thiophene-carboxaldehyde, Adoxal, p-anisaldehyde, Benzylaldehyde, Bourgenal, Cinnamic aldehyde, Cymal, Decyl aldehyde, Floral super, Florhydral, Helional, Lauric aldehyde, Ligustral, Lyral, Melonal, o-anisaldehyde, Pino acetaldehyde, P.T. Bucinal, Thiophene carboxaldehyde, trans-4-Decenal, trans trans 2,4-Nonadienal, Undecyl aldehyde, and mixtures thereof.

In some embodiments, the malodor control composition includes fast reacting volatile aldehydes. "Fast reacting volatile aldehydes" refers to volatile aldehydes that either (1) reduce amine odors by 20% or more in less than 40 seconds; or (2) reduce thiol odors by 20% or more in less than 30 minutes.

In one embodiment, the malodor control composition includes a mixture of the volatile aldehydes listed in Table 1 and referred to herein as Accord A.

TABLE 1

Accord A

| Material | Wt. % | CAS Number | ClogP Group | VP (torr) @25° C. |
|---|---|---|---|---|
| Intreleven Aldehyde | 5.000 | 112-45-8 | 3 | 0.060 |
| Florhydral | 10.000 | 125109-85-5 | 4 | 0.008 |
| Floral Super | 25.000 | 71077-31-1 | 3 | 0.030 |
| Scentenal | 10.000 | 86803-90-9 | 2 | 0.010 |
| Cymal | 25.000 | 103-95-7 | 4 | 0.007 |
| o-anisaldehyde | 25.000 | 135-02-4 | 1 | 0.032 |

In another embodiment, the malodor control composition includes a mixture of the volatile aldehydes listed in Table 2 and referred to herein as Accord B.

TABLE 2

Accord B

| Material | Wt. % | CAS Number | ClogP Group | VP (torr) @25° C. |
|---|---|---|---|---|
| Intreleven Aldehyde | 2.000 | 112-45-8 | 3 | 0.060 |
| Florhydral | 20.000 | 125109-85-5 | 4 | 0.008 |
| Floral Super | 10.000 | 71077-31-1 | 3 | 0.030 |
| Scentenal | 5.000 | 86803-90-9 | 2 | 0.010 |
| Cymal | 25.000 | 103-95-7 | 4 | 0.007 |
| Floralozone | 10.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| o-anisaldehyde | 25.000 | 135-02-4 | 1 | 0.032 |

In another embodiment, the malodor control composition includes a mixture of about 71.2% volatile aldehydes, the remainder being other an ester and an alcohol perfume raw material. This mixture is listed in Table 3 and referred to herein as Accord C.

TABLE 3

Accord C

| Material | Wt. % | CAS Number | ClogP Group | VP (torr) @25° C. |
|---|---|---|---|---|
| Intreleven Aldehyde | 2.000 | 112-45-8 | 3 | 0.060 |
| Florhydral | 10.000 | 125109-85-5 | 4 | 0.008 |
| Floral Super | 5.000 | 71077-31-1 | 3 | 0.030 |
| Scentenal | 2.000 | 86803-90-9 | 2 | 0.010 |
| Cymal | 15.000 | 103-95-7 | 4 | 0.007 |
| Floralozone | 12.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| Flor Acetate | 11.800 | 5413-60-5 | 1 | 0.060 |
| Frutene | 7.000 | 17511-60-3 | 4 | 0.020 |
| Helional | 5.000 | 1205-17-0 | 2 | 0.0005 |
| Bourgeonal | 2.000 | 18127-01-0 | 4 | 0.004 |
| Linalool | 10.000 | 78-70-6 | 3 | 0.050 |
| Benzaldehyde | 0.200 | 100-52-7 | 1 | 1.110 |
| o-anisaldehyde | 15.000 | 135-02-4 | 1 | 0.320 |

Accords A, B, or C can be formulated in with other perfume raw materials in an amount, for example, of about 10% by weight of the malodor control composition. Additionally, the individual volatile aldehydes or a various combination of the volatile aldehydes can be formulated into a malodor control composition. In certain embodiments, the volatile aldehydes may be present in an amount up to 100%, by weight of the malodor control composition, alternatively from about 0.1% to about 100%, alternatively from about 1% to about 100%, alternatively from about 2% to about 100%, alternatively from about 3% to about 100%, alternatively about 50% to about 100%, alternatively about 70% to about 100%, alternatively about 80% to about 100%, alternatively from about 1% to about 20%, alternatively from about 0.1% to about 10%, alternatively from about 1% to about 10%, alternatively from about 0.1% to about 5%, alternatively from about 1% to about 5%, alternatively from about 1% to about 3%, alternatively from about 2% to about 20%, alternatively from about 3% to about 20%, alternatively from about 4% to about 20%, alternatively from about 5% to about 20%, by weight of the composition.

In some embodiments where volatility is not important for neutralizing a malodor, the present invention may include poly-aldehydes, for example, di-, tri-, tetra-aldehydes. Such embodiments may include laundry detergents, additive, and the like for leave-on, through the wash, and rinse-off type of applications.

2. Acid Catalyst

The malodor control composition of the present invention may include an effective amount of an acid catalyst to neutralize sulfur-based malodors. It has been found that certain mild acids have an impact on aldehyde reactivity with thiols in the liquid and vapor phase. It has been found that the reaction between thiol and aldehyde is a catalytic reaction that follows the mechanism of hemiacetal and acetal formation path. When the present malodor control composition contains an acid catalyst and contacts a sulfur-based malodor, the volatile aldehyde reacts with thiol. This reaction may form a thiol acetal compound, thus, neutralizing the sulfur-based odor. Without an acid catalyst, only hemi-thiol acetal is formed.

Suitable acid catalysts have a VP, as reported by Scifinder, in the range of about 0.001 torr to about 38 torr, measured at 25° C., alternatively about 0.001 torr to about 14 torr, alternatively from about 0.001 to about 1, alternatively from about 0.001 to about 0.020, alternatively about 0.005 to about 0.020, alternatively about 0.010 to about 0.020.

The acid catalyst may be a weak acid. A weak acid is characterized by an acid dissociation constant, Ka, which is an equilibrium constant for the dissociation of a weak acid; the pKa being equal to minus the decimal logarithm of Ka. The acid catalyst may have a pKa from about 4.0 to about 6.0, alternatively from about 4.3 and 5.7, alternatively from about 4.5 to about 5, alternatively from about 4.7 to about 4.9. Suitable acid catalyst include those listed in Table 4.

TABLE 4

| Material | VP (torr) @ 25° C. |
| --- | --- |
| Formic Acid | 36.5 |
| Acetic Acid | 13.9 |
| Trimethyl Acetic Acid | 0.907 |
| Phenol (alkaline in liquid apps yet acidic in vapor phase) | 0.610 |
| Tiglic acid | 0.152 |
| Caprylic acid | 0.0222 |
| 5-Methyl thiophene carboxylic acid | 0.019 |
| Succinic acid | 0.0165 |
| Benzoic acid | 0.014 |
| Mesitylenic acid | 0.00211 |

Depending on the desired use of the malodor control composition, one may consider the scent character or the affect on the scent of the malodor control composition when selecting an acid catalyst. In some embodiments of the malodor control composition, it may be desirable to select an acid catalyst that provides a neutral to pleasant scent. Such acid catalysts may have a VP of about 0.001 torr to about 0.020 torr, measured at 25° C., alternatively about 0.005 torr to about 0.020 torr, alternatively about 0.010 torr to about 0.020 torr. Non-limiting examples of such acid catalyst include 5-methyl thiophene carboxaldehyde with carboxylic acid impurity, succinic acid, or benzoic acid.

The malodor control composition may include about 0.01% to about 5%, alternatively about 0.04% to about 1.5%, alternatively about 0.1% to about 1.0%, alternatively about 0.1% to about 0.5%, alternatively about 0.01% to about 0.4%, alternatively about 0.1% to about 0.4%, alternatively about 0.04% to about 1.5%, alternatively about 0.4% of an acid catalyst by weight of the malodor control composition.

In an acetic acid system, the present malodor control composition may include about 0.4% of acetic acid (50:50 TC:DPM, 0.4% acetic acid).

TABLE 5

| Sample Formulated | Actual % acetic acid in DPM | % Butanethiol reduction @ 30 min. |
| --- | --- | --- |
| 50:50 TC:DPM 0% Acetic Acid | 0.00 | 12.00 |
| 50:50 TC:DPM 0.05% Acetic Acid | 0.04 | 14.65 |
| 50:50 TC:DPM 0.1% Acetic Acid | 0.10 | 25.66 |
| 50:50 TC:DPM 0.2% Acetic Acid | 0.42 | 34.68 |
| 50:50 TC:DPM 0.5% Acetic Acid | 1.00 | 24.79 |
| 50:50 TC:DPM 1.0% Acetic Acid | 2.00 | 7.26 |

When an acid catalyst is present with a volatile aldehyde (or RA), the acid catalyst may increase the efficacy of the volatile aldehyde on malodors in comparison to the malodor efficacy of the volatile aldehyde on its own. For example, 1% volatile aldehyde and 1.5% benzoic acid provides malodor removal benefit equal to or better than 5% volatile aldehyde alone.

The malodor control composition may have a pH from about 3 to about 8, alternatively from about 4 to about 7, alternatively from about, alternatively from about 4 to about 6.

3. Optional Ingredients

The malodor control composition may, optionally, include odor masking agents, odor blocking agents, and/or diluents. For example, the malodor control composition may include a mixture of volatile aldehydes for neutralizing a malodor, perfume ionones, and a diluent. Alternatively, the malodor control composition may include 100% volatile aldehydes.

"Odor-masking agents" refer to known compounds (e.g. perfume raw materials) that mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds.

"Odor blocking agents" refer to known compounds that dull the human sense of smell.

Exemplary diluents include dipropylene glycol methyl ether, and 3-methoxy-3-methyl-1-butanol, and mixtures thereof.

The malodor control composition may also, optionally, include perfume raw materials that solely provide a hedonic benefit (i.e. that do not neutralize malodors yet provide a pleasant fragrance). Suitable perfumes are disclosed in U.S. Pat. No. 6,248,135, which is incorporated in its entirety by reference.

Method of Use

The malodor control composition of the present invention may be used in a wide variety of applications that neutralize malodors in the vapor and/or liquid phase. The malodor control composition may be formulated for use in substrates such as plastics, wovens, or non-wovens (e.g cellulose fibers for paper products). Such substrates may be used as pet food packaging; paper towels; tissues; trash bags; diapers, toddler training pants; baby wipes; adult incontinence products; feminine hygiene products such as sanitary napkins and tampons.

In particular, the present invention encompasses a method of neutralizing malodor associated with urine, menses, and/ or feces, comprising contacting said malodor with the absorbent article comprising the malodor control composition of the present invention. Examples of suitable absorbent articles include diapers, toddler training pants, adult incontinence garments, sanitary napkins, pantiliners, interlabial devices, hemorrhoid pads, and the like.

EXAMPLES

Analytical Test—Effect of Volatile Aldehydes on Amine-Based and Sulfur-Based Malodors Malodor standards are prepared by pipeting 1 mL of butylamine (amine-based malodor) and butanethiol (sulfur-based malodor) into a 1.2 liter gas sampling bag. The bag is then filled to volume with nitrogen and allowed to sit for at least 12 hours to equilibrate.

A 1 µL sample of each volatile aldehyde listed in Table 6 and of each Accord (A, B, and C) listed in Tables 1 to 3 is pipeted into individual 10 mL silanized headspace vials. The vials are sealed and allowed to equilibrate for at least 12 hours. Repeat 4 times for each sample (2 for butylamine analysis and 2 for butanethiol analysis).

After the equilibration period, 1.5 mL of the target malodor standard is injected into each 10 mL vial. For thiol analysis, the vials containing a sample+malodor standard are held at room temperature for 30 minutes. Then, a 1 mL headspace syringe is then used to inject 250 µL of each sample/malodor into a GC/MS split/splitless inlet. For amine analysis, a 1 mL headspace syringe is used to inject 500 µL of each sample/malodor immediately into the GC/MS split/splitless inlet. A GC pillow is used for the amine analysis to shorten the run times.

Samples are then analyzed using a GC/MS with a DB-5, 20 m, 1 µm film thickness column with an MPS-2 autosampler equipment with static headspace function. Data is analyzed by ion extraction on each total ion current (56 for thiol and 30 for amine) and the area is used to calculate the percent reduction from the malodor standard for each sample.

Table 6 shows the effect of certain volatile aldehydes on neutralizing amine-based and sulfur based malodors at 40 seconds and 30 minutes, respectively.

TABLE 6

| Perfume Raw Material (R-CHO) | At least 20% butylamine reduction at 40 secs.? | At least 20% butanethiol reduction at 30 mins.? |
|---|---|---|
| 2,4,5 Trimethoxy Benzaldehyde | No | No |
| 2,4,6-Trimethoxy-benzylaldehyde | No | No |
| 2-ethoxy benzylaldehyde | Yes | Yes |
| 2-isopropyl-5-methyl-2-hexenal | Yes | Yes |
| 2-methyl-3-(2-furyl)-propenal | No | No |
| 3,4,5 Trimethoxy Benzaldehyde | No | No |
| 3,4-Trimethoxy-benzylaldehyde | No | No |
| 4-tertbutyl benzylaldehyde | Yes | No |
| 5-methyl furfural | Yes | Yes |
| 5-methyl-thiophene-carboxaldehyde | No | Yes |
| Adoxal | Yes | No |
| Amyl cinnamic aldehyde | No | No |
| Benzylaldehyde | Yes | No |
| Bourgenal | No | Yes |
| Cinnamic aldehyde | Yes | Yes |
| Citronelyl Oxyacetaldehyde | No | No |
| Cymal | Yes | No |
| Decyl aldehyde | Yes | No |
| Floral Super | Yes | Yes |
| Florhydral | Yes | Yes |
| Floralozone | No | No |

TABLE 6-continued

| Perfume Raw Material (R-CHO) | At least 20% butylamine reduction at 40 secs.? | At least 20% butanethiol reduction at 30 mins.? |
|---|---|---|
| Helional | Yes | No |
| Hydroxycitronellal | No | No |
| Lauric aldehyde | Yes | No |
| Ligustral | Yes | No |
| Lyral | Yes | No |
| Melonal | Yes | No |
| Methyl nonyl acetaldehyde | No | No |
| o-anisaldehyde | Yes | Yes |
| p-anisaldehyde | Yes | No |
| Pino acetaldehyde | Yes | Yes |
| P.T. Bucinal | Yes | No |
| Thiophene Carboxaldehyde | Yes | No |
| Trans-4-decenal | Yes | Yes |
| Trans Trans 2,4-Nonadienal | Yes | No |
| Undecyl aldehyde | Yes | No |

Table 7 shows the percent reduction of butylamine and butaniethiol at 40 seconds and 30 minutes, respectively, for Accords A, B, and C.

TABLE 7

| Accord | % reduction of butylamine at 40 secs. | % reduction of butanethiol at 30 mins. |
|---|---|---|
| Accord A | 76.58 | 25.22 |
| Accord B | 51.54 | 35.38 |
| Accord C | 65.34 | 24.98 |

Analytical Test—Effect of Acid Catalysts on Sulfur-Based Malodors

The above analytical test is repeated using samples containing an acid catalyst to test their effect on sulfur-based malodors. Specifically, a 1 µL aliquot of each of the following controls and acid catalyst samples are pipeted into individual 10 mL silanized headspace vials in duplicate: thiophene carboxyaldehyde as a control; a 50/50 mixture of thiophene carboxyaldehyde and each of the following acid catalysts at 0.04%, 0.10%, 0.43% in DPM, 1.02% in DPM, and 2.04% in DPM: phenol, mesitylenic acid, caprylic acid, succinic acid, pivalic acid, tiglic acid, and benzoic acid.

Figure 1:
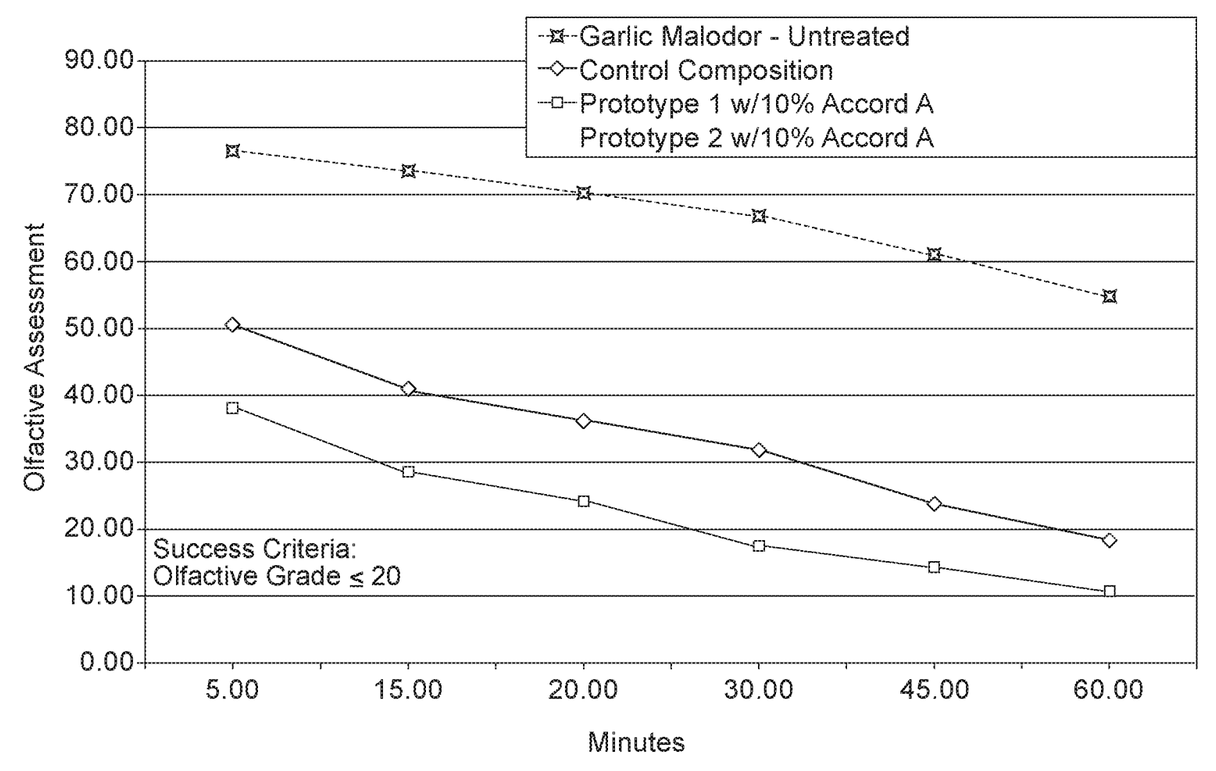
FIG. 1 is a graph showing butanethiol reduction by thiophene carboxaldehyde in combination with various acid catalysts.

FIG. 1 demonstrates that low vapor pressure acid catalysts provide up to 3 times better reduction of sulfur-based malodors in comparison to the control.

Analytical Test—Effect of Volatile Aldehydes and Acid Catalyst on Amine-Based and Sulfur-Based Malodors The above analytical test is repeated using sample formulations containing volatile aldehydes (or RA) and an acid catalyst, as outlined in Tables 8 and 9.

Tables 8 and 9 show that a perfume mixture having as little as 1% volatile aldehyde along with 1.5% acid catalyst performs better at reducing butylamine and butanethiol than the same perfume mixture having 5% volatile aldehyde.

TABLE 8

| Formulation | % butylamine reduction at 40 secs. | | % butanethiol reduction at 30 mins. | |
|---|---|---|---|---|
| Perfume Mixture w/ 5% RA (Control) | 34.21 | — | 2.40 | — |
| Perfume Mixture w/ 1% RA and w/ 1.5% Benzoic Acid | 41.63 | +7.42 | 11.95 | +9.55 |
| Perfume Mixture w/ 3% RA and | 36.19 | +1.98 | 13.56 | +11.16 |

TABLE 8-continued

| Formulation | % butylamine reduction at 40 secs. | | % butanethiol reduction at 30 mins. | |
|---|---|---|---|---|
| w/ 1.5% Benzoic Acid | | | | |
| Perfume A Mixture w/ 5% RA and w/ 1.5% Benzoic Acid | 41.26 | +7.05 | 9.56 | +5.02 |

TABLE 9

| Formulation | % butylamine Reduction at 40 secs. | | % butanethiol reduction at 30 mins. | |
|---|---|---|---|---|
| Perfume mixture w/ 5% RA (Control) | 4.94 | — | 10.52 | — |
| Perfume mixture w/ 1% RA and w/ 1.5% Benzoic Acid | 11.61 | +6.67 | 18.82 | +8.30 |
| Perfume mixture w/ 3% RA and w/ 1.5% Benzoic Acid | 26.89 | +21.95 | 14.85 | +4.33 |
| Perfume mixture w/ 5% RA and w/ 1.5% Benzoic Acid | 20.27 | +15.33 | 16.84 | +6.32 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. An absorbent article comprising a complexed or encapsulated malodor control composition, said malodor control composition comprising:
    at least one volatile aldehyde;
    an acid catalyst having a vapor pressure of about 0.01 to about 13 at 25° C.;
    wherein said at least one volatile aldehyde is present in an amount from about 0.1% to about 5%, by weight of said malodor control composition, and said acid catalyst is present in an amount of about 0.1% to about 1%, by weight of said malodor control composition.

2. The absorbent article of claim 1 wherein said at least one volatile aldehyde has a VP of about 0.001 to about 50 torr.

3. The absorbent article of claim 1 wherein said at least one volatile aldehyde has a VP of about 0.001 torr to about 15 torr.

4. The absorbent article of claim 1 wherein said at least one volatile aldehyde is selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, P.T. bucinal, thiophene carboxaldehyde, trans-4-decenal, trans 2,4-nonadienal, undecyl aldehyde, and mixtures thereof.

5. The absorbent article of claim 1 wherein said at least one volatile aldehyde is selected from the group consisting of flor super, o-anisaldehyde, and mixtures thereof.

6. The absorbent article of claim 1 wherein said at least one volatile aldehyde comprises a mixture of volatile aldehydes selected from the group consisting of Intreleven Aldehyde, Florhydral, 4,8.dimethyl-4,9.decadienal, Scentenal, Cymal, o-anisaldehyde, Floralozone, Adoxal, Methyl Nonyl Acetaldehyde, Melonal, Flor Acetate, Frutene, Helional, Bourgeonal, Linalool, Benzaldehyde, and mixtures thereof.

7. The absorbent article of claim 1 wherein said at least one volatile aldehyde comprises a mixture of volatile aldehydes, said mixture comprising about 0.1% to about 10% of Accord A, by weight of said malodor control composition; wherein Accord A comprises 5% by weight of Intreleven Aldehyde, 10% by weight of Florhydral, 25% by weight of 4,8.dimethyl-4,9.decadienal, 10% by weight of Scentenal, 25% by weight of Cymal, and 25% by weight o-anisaldehyde.

8. The absorbent article of claim 1 wherein said acid catalyst has a vapor pressure of about 0.01 to about 2 torr at 25° C.

9. The absorbent article of claim 1 wherein said acid catalyst is a carboxylic acid.

10. The absorbent article of claim 1 wherein said acid catalyst is present in an amount from about 0.01% to about 0.4%, by weight of said malodor control composition.

11. The absorbent article of claim 1 wherein said acid catalyst is present in an amount of about 0.4%, by weight of said malodor control composition.

12. The absorbent article of claim 1 wherein said composition has a pH of about 4 to about 6.5.

13. The absorbent article of claim 1 further comprising an ingredient selected from the group consisting of: odor masking agents, odor blocking agents, diluents, and mixtures thereof.

14. The absorbent article of claim 1, wherein said absorbent article is selected from the group consisting of a diaper, an adult incontinence garment, a sanitary napkin, a pantiliner, an interlabial device, and a hemorrhoid pad.

15. The absorbent article of claim 1, wherein said absorbent article further comprises a topsheet, a backsheet, and an absorbent core disposed between said topsheet and said backsheet.

16. The absorbent article of claim 15, wherein said absorbent core has a garment-facing side and a body-facing side, and wherein said malodor control composition is disposed on said garment-facing side of said absorbent core.

17. The absorbent article according claim 1, wherein the malodor control composition is starch encapsulated.

18. The absorbent article of claim 1, wherein the malodor control composition is encapsulated in reservoir type capsules and can be released by a mechanical action breaking the shell of the capsule.

19. The absorbent article of claim 1, wherein the malodor control composition is encapsulated in a capsule having a secondary coating material.

20. A method of neutralizing malodor associated with urine, menses, and/or feces, comprising contacting said malodor with the absorbent article of claim 1.

\* \* \* \* \*